United States Patent [19]

Lanzilotta

[11] 4,036,876
[45] July 19, 1977

[54] 18- AND 19-HYDROXYLATED PROSTAGLANDINS

[75] Inventor: Raymond P. Lanzilotta, San Jose, Calif.

[73] Assignee: Syntex (U.S.A.) Inc., Palo Alto, Calif.

[21] Appl. No.: 379,128

[22] Filed: July 13, 1973

[51] Int. Cl.$^2$ .......................................... C07C 177/00
[52] U.S. Cl. ................... 260/514 D; 195/30; 260/468 D; 424/305; 424/317
[58] Field of Search ................. 260/514 D, 168 D

[56] References Cited

U.S. PATENT DOCUMENTS

| | | | |
|---|---|---|---|
| 3,856,852 | 12/1974 | Hsu et al. | 260/514 |
| 3,878,046 | 4/1975 | Marsheck et al. | 195/51 |
| 3,950,406 | 4/1976 | Floyd et al. | 260/514 |

FOREIGN PATENT DOCUMENTS

| | | | |
|---|---|---|---|
| 7,310,276 | 1/1924 | Netherlands | 260/468 |

*Primary Examiner*—Robert Gerstl
*Attorney, Agent, or Firm*—Gerard A. Blaufarb; William B. Walker

[57] ABSTRACT

Novel 18ξ-hydroxylated and 19ξ-hydroxylated prostaglandins and novel microbiological process for the production thereof.

5 Claims, No Drawings

18- AND 19-HYDROXYLATED PROSTAGLANDINS

DESCRIPTION OF THE INVENTION

The present invention relates to novel 18ξ-hydroxylated and 19ξ-hydroxylated prostaglandins and novel microbiological process for the production thereof.

The novel prostaglandin compounds are represented by the following formulas:

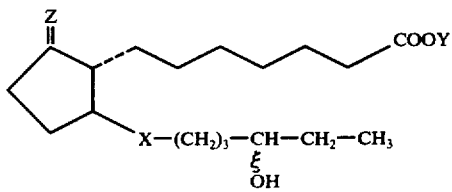

(I)

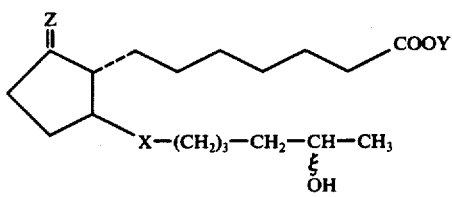

(II)

wherein X is selected from the group consisting of a cis or trans unsaturated carbon-carbon double bond, —CH=CH—; Z is selected from the group consisting of keto and

Y is selected from the group consisting of hydrogen, a lower alkyl group or a pharmaceutically acceptable salt; and the wavy line (ξ) represents a mixture of the (R) and (S) antimers.

Prostaglandins are members of a new hormonal system with a remarkable range of bilogical and pharmaceutical properties. These compounds belong to a group of chemically related 20-carbon chain hydroxy fatty acids containing a five membered ring in the structure and different degrees of unsaturation, a number of which have been reported in the literature. For a review on prostaglandins and the definition of primary prostaglandins, see for example, S. Bergström, *Recent Progress in Hormone Research*, 22, pp. 153–175 (1966) and *Science*, 157, page 382 (1967) by the same author.

Prostaglandins are widely distributed in mammalian tissues and have been isolated from natural sources in very small amounts. In addition, a number of the naturally occurring prostaglandins have been prepared by chemical synthesis; note for example, *J. Am. Chem. Soc.*, 91, page 5675 (1969); *J. Am. Chem. Soc.*, 92, page 2586 (1970) and *J. Am. Chem. Soc.*, 93, pages 1489–1493 (1971) and references cited therein, W. P. Schneider et al., *J. Am. Chem. Soc.*, 90, page 5895 (1968); U. Axen et al., *Chem. Commun.*, page 303 (1969) and W. P. Schneider, *Chem. Commun.*, page 304 (1969).

Because of the remarkable range of biological and pharmacological properties exhibited by this family of compounds, a great deal of interest has focused upon such compounds, and the preparation of analogs of such compounds; accordingly, I have discovered novel prostaglandins and a microbiological process for the preparation thereof.

The novel prostaglandin compounds of Formulas (Ia, Y=H) and (IIa, Y=H), depicted more fully below, are obtained by subjecting the compounds of Formula (A),

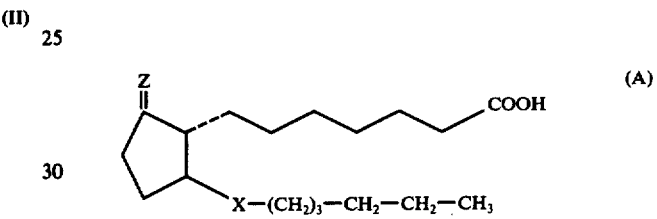

(A)

wherein X, Z and the wavy line (ξ) have the meanings previously given, to the oxidative action of a suitable microorganism or enzymes thereof of *Microascus trigonosporus*.

Specific microorganisms particularly suitable for use in the process of this invention are *Microascus trigonosporus* NRRL 1570 and *Microascus trigonosporus* NRRL 1660.

Suitable substrates embraced by Formula (A) are:

1. 9-keto-prosta-13-cis-enoic acid [see Alvarez et al. JACS, 94, 7823 (1972)], 2. 9-keto-prosta-13-trans-enoic acid [see Sih et al., Tetrahedron Letters, No. 24, p. 2435 (1972)], 3. 9ξ-hydroxyprosta-13-cis-enoic acid, and 4. 9ξ-hydroxyprosta-13-trans-enoic acid.

The 9ξ-hydroxy substrates, (3) and (4), are prepared from the 9-keto compounds, (1) and (2), respectively, by methods known in the art for the reduction of a keto group to a hydroxy group. Thus, for example, the 9-keto compounds, (1) and (2), are reduced with sodium borohydride in tetrahydrofuran (as described more fully in Preparation 1) to obtain the 9ξ-hydroxy compounds, (3) and (4), respectively.

The preparation of the compounds of Formulas (Ia, Y=H) and (IIa, Y=H) from the substrate componds of Formula (A) can be depicted schematically as follows:

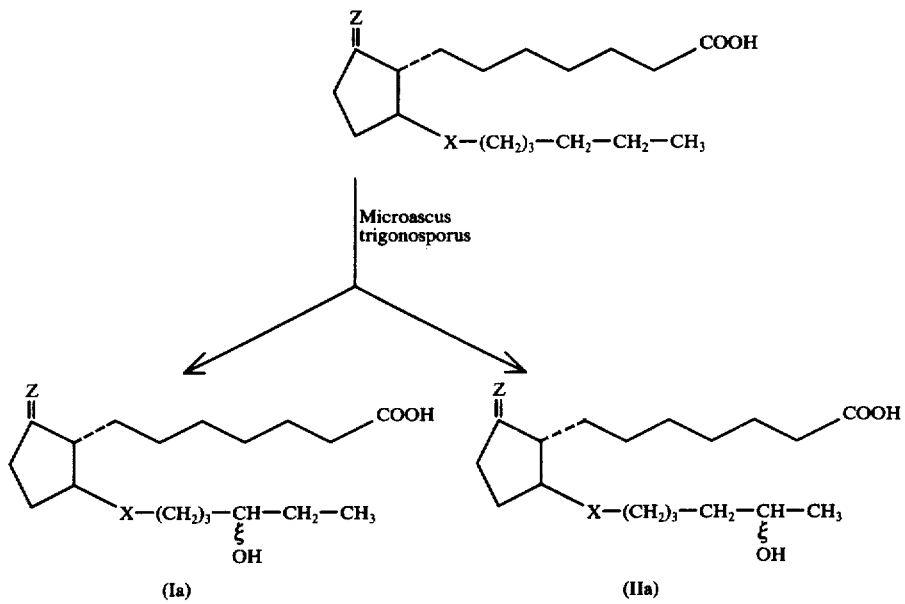

wherein X is selected from the group consisting of cis or trans carbon-carbon double bonds, —CH=CH—; Z is selected from the group consisting of keto and HO
  H;

and the wavy line (ξ) represents a mixture of the (R) and (S) antimers.

In the practice of this invention, the oxidative conversion of the compounds of Formula (A) to the compounds of Formulas (Ia) and (IIa) may be effected in the growing culture of the microorganism either by adding the substrate to the culture during the incubation period or by including it in the nutrient medium prior to inoculation. Assimilable sources of carbon and nitrogen should be present in the culture medium. An adequate sterile air supply should be maintained during the conversion, for example, by the conventional techniques either of exposing a large surface of the medium to the sterile air or by passing air through a submerged culture.

Sources of nitrogenous growth-promoting factors are those normally employed in such processes. They may be natural organic materials such as soybean meal, corn steep liquor, meat extracts, peptone and/or distiller's solubles or synthetics such as nitrates and ammonium compounds.

Suitable energy source materials which may be utilized in the process of this invention include meat extracts, peptone, and the like, which serve also as nitrogen sources, or other conventional carbon-containing materials such as carbohydrates of the type exemplified by glycerol, glucose, fructose, dextrose, sucrose, lactose, maltose, dextrins, starches and whey. These materials may be used either in purified states or as concentrates, such as whey concentrate, corn steep liquor, grain mashes, and the like, or as mixtures of the above.

Along with the sources of carbon and nitrogen present in the nutrient medium there are also advantageously present salts which provide various non-toxic elements, e.g., sodium, potassium, magnesium, calcium, iron, and the like, and non-toxic trace elements, e.g., boron, manganese, zinc, copper and molybdenum, and the like.

The preferred but not limiting range of concentration of the substrate in the culture is about 0.01 to 1.0%. The time interval required for action of the enzyme system of the microorganisms employed may vary depending on the substrate concentration employed, the range of 12–120 hours being practical but not limiting. The process of the present invention may be conducted at temperatures of 22° to 35° C, the range of 28° to 30° C being particularly preferred. It has been determined that the substrate can be conveniently added to the reaction medium dissolved in a suitable organic solvent such as ethanol, acetone, dimethylformamide, and the like, with ethanol being preferred.

The compounds of Formulas (Ia) and (IIa) can be recovered, purified and/or separated from each other by conventional procedures known to those skilled in the art, e.g., extraction with a water immiscible organic solvent, ion exchange chromatography, thin-layer chromatography, absorption chromatography, and the like, or a combination of these.

The alkyl esters are obtained by treatment of the compounds of Formulas (Ia) and (IIa) with an excess of a diazoalkane such as diazomethane, diazoethane or diazopropane in ether or methylene chloride solution, in a conventional manner.

Alternatively, the mixture of 18ξ- hydroxylated compounds, Formula (Ia), and 19ξ-hydroxylated compounds, Formula (IIa), can be esterified as described immediately above, and the 18ξ-hydroxy- and 19ξ-hydroxy-alkyl esters recovered, purified and/or or separated, according to procedures described above for the compounds of Formulas (Ia) and (IIa).

The salt derivatives of the acids of Formulas (Ia) and (IIa) are prepared by treating the corresponding free acids with about one molar equivalent of a pharmaceutically acceptable base. Representative pharmaceutically acceptable bases are sodium hydroxide, potassium hydroxide, ammonium hydroxide, calcium hydroxide, trimethylamine, triethylamine, tripropylamine, β-(dimethylamino) ethanol, β-(diethylamino) ethanol, arginine, lysine, caffeine, procaine and the like. The reaction is conducted in an aqueous solution, alone or in combination with an inert, water miscible organic solvent, at a temperature of from about 0° C to about 30° C, preferably at room temperature. Typical inert, water miscible organic solvents include methanol, ethanol, isopropanol, butanol, dioxane or tetrahydrofuran. When divalent metal salts are prepared, such as the calcium salts or magnesium salts, the free acid starting material is treated with at least one half molar equivalent of the pharmaceutically acceptable base.

The free acids, esters and salts of the invention, the compounds of Formulas (I) and (II), exhibit prostaglandin-like biological activities and thus are useful in the treatment of mammals where the use of prostaglandins is indicated. They are bronchodilators and thus are useful in treating mammals for bronchial spasm or wherever strong bronchodilators are indicated. These compounds are also useful in controlling or palliating hypertension in mammals and further exhibit central nervous system depressant activity in mammals, and are useful as sedatives. In addition, the compounds are useful for inducing labor, in pregnancy, and for inducing menses to correct or reduce menstrual abnormalities.

The free acids, esters or salts of Formulas (I) and (II) can be administered in a wide variety of dosage forms, either alone or in combination with other pharmaceutical compatible medicaments, in the form of pharmaceutical compositions suited for oral or parenteral administration or inhalation in the case of bronchodilators. The compounds are typically administered as pharmaceutical compositions consisting essentially of the free acids, esters of the invention, and a pharmaceutical carrier. The pharmaceutical carrier can be either a solid material, liquid or aerosol, in which the free acid, ester or salt is dissolved, dispersed or suspended, and can optionally contain small amounts of preservatives and/or pH-buffering agents. Suitable preservatives which can be used include, for example, benzyl alcohol and the like. Suitable buffering agents include, for example, sodium acetate and pharmaceutical phosphate salts and the like.

The liquid compositions can, for example, be in the form of solutions, emulsions, suspensions, syrups, or elixirs. The solid compositions can take the form of tablets, powders, capsules, pills or the like, preferably in unit dosage forms for simple administration or precise dosages. Suitable solid carriers include, for example, pharmaceutical grades of starch, lactose, sodium saccharin, talcum, sodium bisulfite and the like.

For inhalation administration, the free acids, esters or salts can, for example, be administered as an aerosol in an inert propellant together with a cosolvent, e.g., ethanol, together with optional preservatives and buffering agents. Additional general information concerning the inhalation administration of aerosols can be had by reference to U.S. Pat. Nos. 2,868,691 and 3,095,355.

The free acids, esters or salts of Formulas (I) and (II) are typically administered in dosages of about from 0.01 to 10 mg. per kg. of body weight. The precise effective dosage will, of course, vary depending upon the type of compound being administered (free acid, ester or salt), the mode of administration (oral or parenteral), condition being treated and host.

A further understanding of the invention can be had from the following non-limiting preparations and examples.

PREPARATION 1

A solution of 200 mg. of 9-keto-prosta-13-cis-enoic acid in 10 ml. of tetrahydrofuran is cooled to 0° C and treated with 100 mg. of sodium borohydride dissolved in one ml. of water. The reaction mixture is stirred at room temperature for 30 minutes and thereafter most of the solvent is eliminated under vacuum. Water is added to the residue and the product extracted with ethyl acetate. The organic extract is washed with water, dilute hydrochloric acid solution and water to neutrality, dried over magnesium sulfate and evaporated to dryness under vacuum to yield 9$\xi$-hydroxyprosta-13-cis-enoic acid.

Similarly, substituting 9-keto-prosta-13-trans-enoic acid is productive of 9$\xi$-hydroxyprosta-13-trans-enoic acid.

PREPARATION 2

An agar slant of *Microascus trigonosporus* NRRL 1570 is prepared using the following medium:

Medium 1

| | |
|---|---|
| Glucose | 20 g. |
| Malt Extract | 20 g. |
| Peptone | 1 g. |
| Agar | 15 g. |
| Distilled Water | 1000 ml. |

After being incubated at 28° C for two weeks, the surface growth is harvested and used to inoculate two 250 ml. Erlenmeyer flasks each of which contains 50 ml. of the following medium:

Medium 2

| | |
|---|---|
| Glucose (Cerelose) | 30 g. |
| Soybean Meal | 5 g. |
| Yeast Extract | 5 g. |
| NaCl | 5 g. |
| $K_2HPO_4$ | 5 g. |
| Distilled Water | 1000 ml. |

Prior to inoculation, Medium 2 is adjusted to pH 6.5 by the addition of hydrochloric acid and sterilized.

The inoculated flasks are incubated on a rotary shaker (280 rpm with a one inch stroke) at 28° C for 72 hours.

Twenty 250 ml. Erlenmeyer flasks containing 50 ml. of a sterilized mineral salts medium of the following composition:

Medium 3

| | |
|---|---|
| Glucose | 20.0 g. |
| $NaH_2PO_4 \cdot H_2O$ | 1.2 g. |
| $K_2HPO_4 \cdot 3H_2O$ | 0.25 g. |
| $NH_4NO_3$ | 0.20 g. |
| $MgSO_4$ | 0.05 g. |
| $CaCl_2$ | 0.01 g. |
| $Fe(NH_4)(SO_4)_2 \cdot 6H_2O$ | 0.0005 g. |
| Trace element solution | 1.0 ml. |
| Distilled $H_2O$ | 1000 ml. | are then each inoculated with 5 ml. of the thus-obtained 72 hour culture. These inoculated flasks are incubated on a rotary shaker, as described above, for 24 hours.

The trace element solution used in Medium 3 contains per liter of water the following:

| | |
|---|---|
| $H_3BO_3$ | 2.86 g. |
| $MnCl_2 \cdot 4H_2O$ | 1.18 g. |
| $ZnSO_4 \cdot 7H_2O$ | 0.22 g. |
| $CuSO_4 \cdot 5H_2O$ | 0.08 g. |
| $H_2MoO_4 \cdot H_2O$ | 0.02 g. |

EXAMPLE 1

To 10 of the flasks, containing *Microascus trigonosporus* NRRL 1570, prepared as described in Preparation 2, there is added 12.5 mg. of 9-keto-prosta-13-cis-enoic acid in 0.4 ml. of ethanol. The flasks are incubated for 48 hours on a rotary shaker (280 rpm with a one inch stroke) at 28° C, after which the contents of the flasks are combined, acidified with phosphoric acid to approximately pH 3, and extracted with three 250 ml. portions of chloroform. The chloroform extracts are combined, dried over anhydrous sodium sulfate, followed by stripping of the chloroform under vacuum to yield a residue containing 9-keto-18ξ-hydroxyprosta-13-cis-enoic acid and 9-keto-19ξ-hydroxyprosta-13-cis-enoic acid.

The residue is taken up in a minimum volume of chloroform, streaked on preparative silica gel thin-layer chromatography plates and developed with benzene:tetrahydrofuran:formic acid (80:2:1; by volume). The less polar (faster moving) 18ξ-hydroxylated derivative separates from the more polar (slower moving) 19ξ-hydroxylated derivative and the separated compounds are recovered from the silica gel by elution with methanol to yield 9-keto-18ξ-hydroxyprosta-13-cis-enoic acid and 9-keto-19ξ-hydroxyprosta-13-cis-enoic acid.

Similarly, substituting 9ξ-hydroxyprosta-13-cis-enoic acid for 9-keto-prosta-13-cis-enoic acid, in the above procedure, is productive of 9ξ,18ξ-dihydroxyprosta-13-cis-enoic acid, and 9ξ,19ξ-dihydroxyprosta-13-cis-enoic acid.

EXAMPLE 2

To 10 of the flasks, containing *Microascus trigonosporus* NRRL 1570, prepared as described in Preparation 2, there is added 12.5 mg. of 9-keto-prosta-13-trans-enoic acid in 0.4 ml. of ethanol. The flasks are incubated for 48 hours on a rotary shaker (280 rpm with a one inch stroke) at 28° C, after which the contents of the flasks are combined, acidified with phosphoric acid to approximately pH 3, and extracted with three 250 ml. portions of chloroform. The chloroform extracts are combined, dried over anhydrous sodium sulfate, followed by stripping of the chloroform under vacuum to yield a residue containing 9-keto-188ξ-hydroxyprosta-13-trans-enoic acid and 9-keto-19ξ-hydroxyprosta-13-trans-enoic acid.

The residue is taken up in a minimum volume of chloroform streaked on preparative silica gel thin-layer chromatography plates and developed with benzene:tetrahydrofuran:formic acid (80:20:1; by volume). The less polar (faster moving) 18ξ-hydroxylated derivative separates from the more polar (slower moving) 19ξ-hydroxylated derivative and the separated compounds are recovered from silica gel by elution with methanol to yield 9-keto-18ξ-hydroxyprosta-13-trans-enoic acid and 9-keto-19ξ-hydroxyprosta-13-trans-enoic acid.

Similarly, substituting 9ξ-hydroxyprosta-13-trans-enoic acid for 9-keto-prosta-13-trans-enoic acid, in the above procedure, is productive of 9ξ,18ξ-hydroxyprosta-13-trans-enoic acid, and 9ξ,19ξ-dihydroxyprosta-13-trans-enoic acid.

EXAMPLE 3

To a solution of 100 mg. of 9-keto-18ξ-hydroxyprosta-13-cis-enoic acid in 5 ml. of methylene chloride is added an ethereal solution of diazomethane until the color of the reagent persists in the mixture. The reaction mixture is maintained at room temperature for 1 hour and is then evaporated to dryness under reduced pressure, thus yielding 9-keto-18ξ-hydroxyprosta-13-cis-enoic acid methyl ester.

In a similar manner,
9-keto-19ξ-hydroxyprosta-13-cis-enoic acid,
9ξ,18ξ-dihydroxyprosta-13-cis-enoic acid,
9ξ,19ξ-dihydroxyprosta-13-cis-enoic acid,
9-keto-18ξ-hydroxyprosta-13-trans-enoic acid,
9ξ,18ξ-dihydroxyprosta-13-trans-enoic acid,
9ξ,19ξ-dihydroxyprosta-13-trans-enoic acid,
are converted into their corresponding methyl esters.

Likewise, the ethyl esters of the foregoing acids are produced using diazoethane in lieu of diazomethane.

EXAMPLE 4

To a solution of 100 mg. of 9-keto-18ξ-hydroxyprosta-13-cis-enoic acid in 10 ml. of methanol is added 2.6 ml. of a 0.1N solution of sodium hydroxide, and the mixture is stirred at room temperature for 1 hour. It is then evaporated to dryness under reduced pressure to give the sodium salt of 9-keto-18ξ-hydroxyprosta-13-cis-enoic acid.

By employing 1.1 molar equivalents of potassium hydroxide (in the form of a 0.1N solution) in place of sodium hydroxide in the above procedure the potassium salt of 9-keto-18ξ-hydroxyprosta-13-cis-enoic acid is obtained.

Similarly, the sodium and potassium salts of the other prostaenoic acid derivatives obtained in Examples 1 and 2 are produced.

EXAMPLE 5

To a solution of 100 mg. of 9-keto-18ξ-hydroxyprosta-13-cis-enoic acid in 10 ml. of methanol is added a mixture of 3 ml. of concentrated ammonium hydroxide solution and 5 ml. of methanol. The resulting mixture is stirred for two hours at room temperature and then evaporated to dryness to yield the ammonium salt of 9-keto-18ξ-hydroxyprosta-13-cis-enoic acid.

By employing dimethylamine, diethylamine or dipropylamine in place of ammonium hydroxide in the above process the corresponding salts of 9-keto-18ξ-hydroxyprosta-13-cis-enoic acid are obtained.

In a similar manner, the ammonia, dimethylamine, diethylamine and dipropylamine salts of the other prostaenoic acids derivatives of Examples 1 and 2 are prepared.

Obviously many modifications of the invention, described herein above and below in the claims, can be made without departing from the essence and scope thereof.

What is claimed is:
1. The compounds of the formulas:

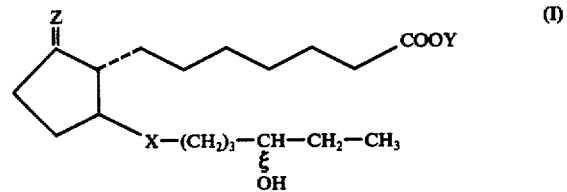

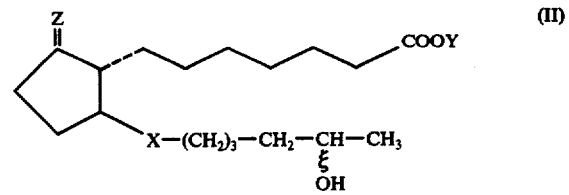

wherein X is a cis unsaturated carbon-carbon double bond, —CH=CH—;
Y is selected from the group consisting of hydrogen, lower alkyl or a pharmaceutically acceptable salt;
Z is selected from the group consisting of keto and

and the wavy line (ξ) is a mixture of the (R) and (S) antimers.

2. The compound of Formula (I) of claim 1 wherein X is a cis unsaturated carbon-carbon double bond and Z is keto, 9-keto-18ξ-hydroxyprosta-13-cis-enoic acid.

3. The compound of Formula (II) of claim 1 wherein X is a cis unsaturated carbon-carbon double bond and Z is keto, 9-keto-19ξ-hydroxyprosta-13-cis-enoic acid.

4. The compound of Formula (I) of claim 1 wherein X is a cis unsaturated carbon-carbon double bond and Z is

9ξ,18ξ-dihydroxyprosta-13-cis-enoic acid.

5. The compound of Formula (II) of claim 1 wherein X is a cis unsaturated carbon-carbon double bond and Z is

9ξ,19ξ-dihydroxyprosta-13-cis-enoic acid.

* * * * *